United States Patent [19]

Broeze et al.

[11] Patent Number: 4,999,194
[45] Date of Patent: Mar. 12, 1991

[54] TWO-CHAIN UROKINASE PLASMINOGEN ACTIVATORS FOR TREATMENT OF THROMBOTIC DISEASE

[75] Inventors: Robert J. Broeze, Framingham; Gerald F. Vovis, Marlborough, both of Mass.

[73] Assignee: Collaborative Research, Inc., Bedford, Mass.

[21] Appl. No.: 143,975

[22] Filed: Jan. 14, 1988

[51] Int. Cl.$^5$ .................. C12N 9/72; A61K 37/547
[52] U.S. Cl. .................... 424/94.63; 435/215; 435/226; 435/212
[58] Field of Search ............. 435/212, 215, 226, 214, 435/172.3; 424/94.63; 935/10, 14

[56] References Cited

U.S. PATENT DOCUMENTS 4,766,075  8/1988  Goeddel et al. ............... 435/240.2

FOREIGN PATENT DOCUMENTS 0092182  10/1983  European Pat. Off. ......... 435/172.3
0196920  10/1986  European Pat. Off. ............ 435/215

OTHER PUBLICATIONS

Ichinose et al., J. Biol Chem., vol. 261, pp. 3486–3489, 1986.
Van Zonneveld et al., Proc. Natl. Acad. Sci., vol. 83, pp. 4670–4674, 1986.
Holmes, W. et al, Bio./Technology, vol. 3, pp. 923–929, 1985.
Rijken et al., J. Biol. Chem., vol. 256, pp. 7035–7041, 1981.
Lijnen, et al., Eur. J. Biochem., vol. 169, pp. 359–364, 1987.
Lijnen, et al., J. Biol. Chem., vol. 261, pp. 1253–1258, 1986.

Primary Examiner—Richard A. Schwartz
Assistant Examiner—Marianne Porta
Attorney, Agent, or Firm—Wolf, Greenfield & Sacks

[57] ABSTRACT

A fibrin specific two-chain plasminogen activator in a therapeutic dosage form. A method is also provided for dissolving clots in vivo by application to the body of a fibrin specific two-chain plasminogen activator in therapeutic dosage form.

7 Claims, 2 Drawing Sheets

TWO-CHAIN UROKINASE PLASMINOGEN ACTIVATORS FOR TREATMENT OF THROMBOTIC DISEASE

FIELD OF INVENTION

This invention concerns a therapeutic plasminogen activator useful to dissolve unwanted clots in the body.

BACKGROUND OF THE INVENTION

Recently, much attention has focused on the therapeutic potential for the individual components of the fibrinolytic system and especially for the plasminogen activators because they can control the initiation of the process.

Thrombolytic therapy is usually carried out with urokinase, a serine protease isolated from human urine, or streptokinase, a bacterial protein. Both of these plasminogen activators can activate plasminogen to form plasmin and are employed in clinical practice today. However, urokinase has a very short (3-15 minutes) useful half-life following its injection into humans since it exists in an enzymatically fully active form which is inactivated by the relatively high concentrations of protease inhibitors in the body fluids. The short half-life for this material has required that large amounts of urokinase be infused during therapeutic treatment.

Since it is easier to obtain and far less expensive than urokinase, streptokinase is the most widely used thrombolytic agent at present. However, its use in thrombolytic therapy is limited due to its bacterial origin. Streptokinase is a plasminogen activator produced by Lancefield group C strains of beta-hemolytic streptococci. Unlike urokinase which directly activates plasminogen to plasmin, streptokinase activates the fibrinolytic system indirectly by complexing with plasminogen to produce an active modified plasminogen moiety. Thrombolysis with both of these substances, urokinase and streptokinase, however, is usually associated with systemic activation of plasminogen which can produce indiscriminate digestion of circulating coagulation proteins such as fibrinogen and alpha-2-antiplasmin, and significantly increase the risk of haemorrhage during treatment. Thus, these agents are said to lack thrombolytic selectivity or fibrin specificity in their activation of plasminogen.

Plasminogen activators have been extracted from normal and tumor tissues and are produced by certain cells in culture. The plasminogen activators derived from these sources are serine proteases with a high thrombolytic selectivity or fibrin specificity in their plasminogen activation. Thus, these activators convert plasminogen to plasmin in a selective manner, causing lysis of fibrin clots while preserving much of the circulating coagulation proteins. There are two types of plasminogen activators with high thrombolytic selectivity—a single-chain urokinase-type plasminogen activator (scu-PA) also known as prourokinase (PUK), and tissue-type plasminogen activator (TPA)—which are easily distinguished by differences in their immunological properties. The single-chain urokinase-type plasminogen activator (scu-PA) is a trypsin-like serine protease 411 amino acid residues in length. The molecule contains three domains: a cysteine-rich amino-terminal region of 45 amino acid residues which is homologous with epidermal growth factor (EGF) and thus is termed the EGF domain; a kringle region or kringle domain which comprises the 87 amino acid residues immediately adjacent to the EGF domain; and a serine protease region, with the active site residues histidine, aspartate and serine, in the carboxy-terminal region of the molecule.

Tissue type plasminogen activator (TPA) is also a serine protease and is composed of a single polypeptide chain of 527 amino acids. The primary structure of TPA shares a high degree of homology with that of scu-PA. For example, TPA is converted by plasmin cleavage of the arginine 275-isoleucine 276 bond to a two chain form also linked by at least one disulfide bond. However, unlike scu PA, TPA is not cleaved by thrombin (Ichinose et al., 1986. J. Biol. Chem. 261, 3486–3489).

Single chain uPA (scu-PA) has been shown to be an effective and fibrin selective plasminogen activator by measurements of preservation of the circulating coagulation proteins fibrinogen and alpha-2-antiplasmin during clot lysis in vivo in a rabbit model system (Stump et al., 1987, *Blood* 69: 592–596) and in a dog model system (Collen et al., 1985, *Circulation* 72: 384–388). By contrast plasmin-generated tcu-PA (cleaved at the lysine 158-isoleucine 159 peptide bond) is less effective in vivo and considerably less fibrin selective.

Hydrolysis of the lysine 158-isoleucine 159 bond by plasmin converts the single chain scu-PA into urokinase, a two chain scuPA (plasmin generated tcu-PA) in which the chains are linked to one another by at least one disulfide bridge. In addition, purified human thrombin recently has been shown to cleave the arginine 156 phenylalanine 157 bond to yield a similar but different two-chain uPA, a thrombin-generated tcu PA in which the chains are also held together by at least one disulfide bond (Ichinose et al., 1986. J. Biol. Chem. 261, 3486–3489). A preparation of enzymes from the venom of the snake *Agkistrodon contortrix* produces two chain u-PA with identical properties as measured in vitro (Gurewich and Pannell, 1987. Blood, 69, 769–772), and may result from cleavage of the same arginine 156 phenylalanine 157 bond.

Both cleavage by plasmin and cleavage by thrombin may play important physiological roles and have been demonstrated to produce molecules with quite different properties as measured in vitro. For example, plasmin cleavage produces a tcu-PA which is more active than scu-PA on small molecule substrates such as S2444 (N-pyro-Glu-Gly-p-nitroanilide), while thrombin cleavage produces a tcu-PA which is inactive on S2444 and which currently is considered to be non-cleavable by plasmin (Ichinose et al., 1986, *supra*; Gurewich and Pannell, 1987, *supra*). The properties of plasmin-produced tcu-PA (ie., urokinase) as measured in in vivo thrombolytic systems reveal it to be inferior to scu-PA with regard to efficiency of clot lysis (potency) and fibrin specificity (Stump et al., 1987, *Blood* 69: 592–596; Collen et al., 1985, *Circulation* 72: 384–388). In contrast, nothing is known about the properties of thrombin-generated tcu-PA in in vivo thrombolytic systems. Current theory holds that fibrin-specificity is a property of single-chain full length u-PA and single-chain truncated u-PA (scu-PA-32k) beginning with leucine residue 144 (Stump et al., 1987, *supra*). Consistent with this notion, plasmin generated tcu-PA (ie., urokinase) lacks fibrin-specificity in its initation of clot lysis in vitro and in vivo. At present, no two-chain urinary plasminogen activators are generally known to the field to have fibrin-specificity. Thrombin-generated tcu-PA has been considered inactive and unactivable; indeed, the generation of tcu PA cleaved by thrombin has been regarded as a normal physiological mechanism for preventing formation of plasmin-generated tcu-PA and thereby down-modulating the activity of scu-PA (Gurewich and Pannell, 1987, *supra*).

Unexpected new uses of the thrombin-generated tcu-PA molecule which permit use in therapeutic methods of treatment for pulmonary embolism, deep vein thrombosis, heart attack and stroke, have been discovered and are the subject of the present invention. These new uses include efficient clot lysis in vivo with a high degree of fibrin specificity. Thus, a plasminogen activator useful for thrombolysis has been made available as a new therapeutic agent.

SUMMARY OF THE INVENTION

It is an object of the present invention to provide a two-chain uPA which exhibits efficient fibrin specific thrombolysis in vivo and can be provided in a therapeutic dose form.

A further object of the present invention is to provide means and methods for producing and using the fibrin-specific tcu-PA of the preceding object as a therapeutic agent in man.

The fibrin-specific tcu-PA of this invention can be formulated as a therapeutic dose and injected into blood in the body in vivo at a dosage level sufficient to dissolve clots without causing unwanted body change. Typical parameters for its use in the treatment of myocardial infarction can be as known and described previously for streptokinase and tissue-type plasminogen activator as for example in (Van de Werf, et al., 1984, *N.E. Jour. Med.* 310: 609–613; TIMI Phase I Findings, 1985, *N.E. Jour. Med.* 312: 932–936).

The present invention is directed to the therapeutic use of an enzyme cleaved tcu-PA which surprisingly exhibits activity on par with human prourokinase first isolated by Husain, S. S., Lipinski, B., and Gurewich, V. (U.S. Pat. No. 4,381,346). According to the present invention, tcu-PA produced by cleavage with thrombin or other enzyme at the arginine 156-phenylalanine 157 peptide bond unexpectedly exhibits efficient clot lysis and high fibrin selectivity when used in vivo. Cleavage can also be carried out at any of the 149 to 155 peptide bonds.

DESCRIPTION OF PREFERRED EMBODIMENTS

Tcu-PA which is cleaved at the arginine 156-phenylalanine 157 peptide bond is both effective and fibrin selective during clot lysis in vivo.

Figure 1:
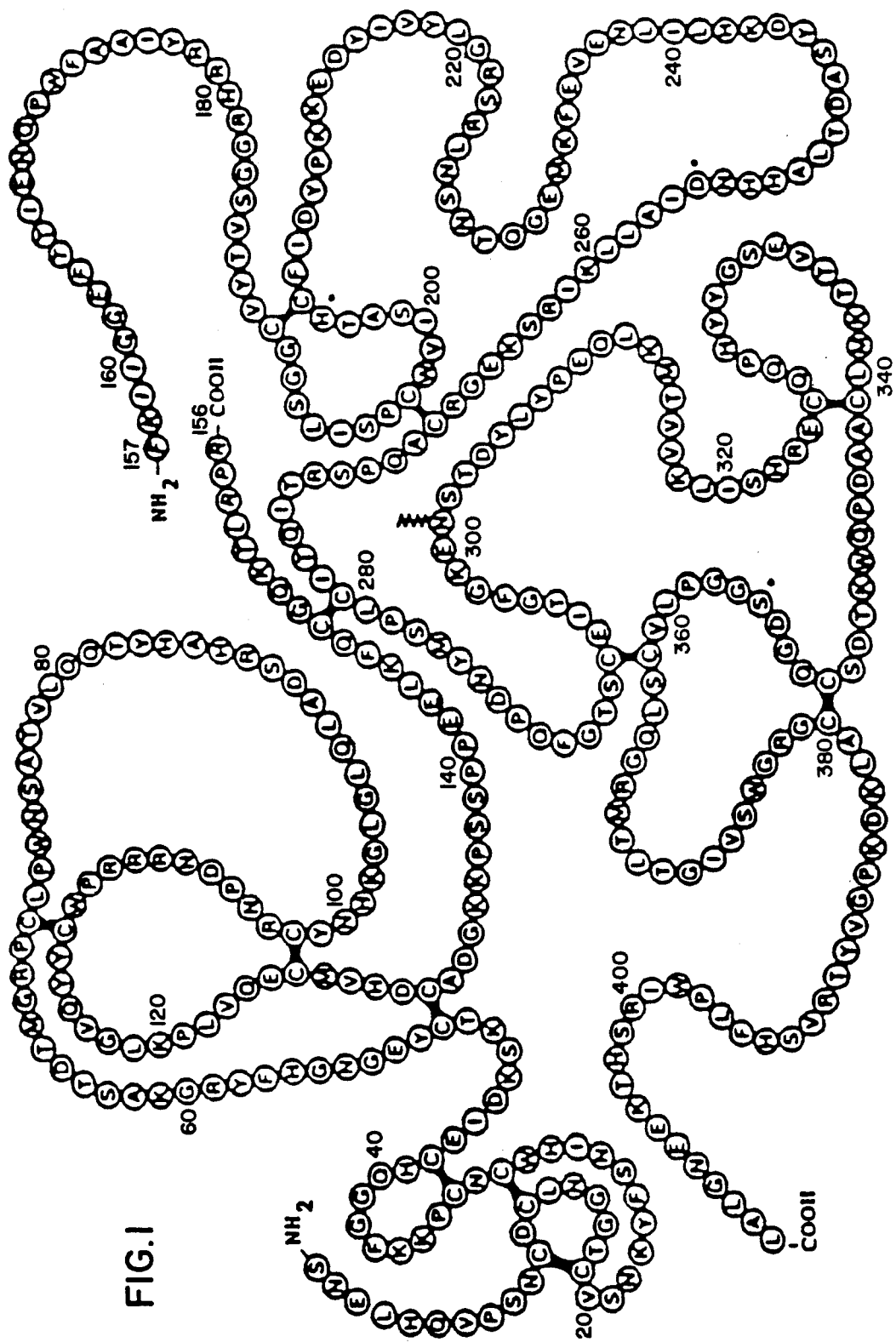
FIG. 1 is a two-dimensional illustration of the structure of thrombin-cleaved scu-PA (modified from the schematic drawing of scu-PA by Holmes et al., 1985, *Biotechnology* 3: 923–929). The new carboxy and amino termini resulting from thrombin cleavage are shown at amino acid residues 156 and 157 respectively; and, FIG. 2 is a graphic illustration of the results obtained and specified in Table 1.

Such two-chain urokinase is illustrated in FIG. 1 and is known in the art. However, the structures known in the art have been experimental only and have not been used as therapeutic doses nor have they been recognized to have any properties suitable for therapeutic or in vivo clot lysis use. It is now the object of this invention to provide such two-chain urokinase for use in therapeutic dosage formulations. For example, in the treatment of myocardial infarct the tcu-PA can be provided to human patients at doses of from about 0.1 to about 4 milligrams per kilogram of body weight and higher in some cases, without loss of fibrin specificity in its action.

Dosage forms can have tcu-PA at concentrations of from about 0.1 mg/ml to about 10.0 mg/ml or higher in carriers such as manitol, aqueous sodium chloride, human serum albumin or other known excipients. The dose may be provided by intravenous infusion for up to six hours. Alternate methods of application can include providing the doses in intravenous bolus followed by intravenous infusion of the remainder for long time periods as for example six hours. It may in addition be provided with various excipients as for example in normal saline, glucose or other carriers with or without additional therapeutic materials. For example, antibiotics, antiviral and anti-infection agents can be used along with the material of this invention. Injection and introduction into the body can be accomplished by any of the known means for introducing a material into the blood stream. Dosage rates can vary depending upon the particular treatment to be made For example, lysis of clots can be accomplished in various areas of the body including the brain, deep veins, coronary arteries and the like as is known in the art. In general, the material of this invention can be used in the same manner as known with use for streptokinase and tissue plasminogen activator.

Dosage forms for use in this invention are formulated using known pharmaceutical methods and procedures. In all cases, the dosage forms are viral free and preferably a bacteria free environment is preferred, i.e., at least no pathogens are contained in the dosage units. The actual mounts and forms of dosage units can vary. In some cases, powdered forms can be used while in others, the dosages are provided in liquid suspensions. Conventional vials, capsules and the like can be used.

The following examples are illustrative of the invention but are not to be considered as limiting thereof. These examples relate to the preparation of thrombin-cleaved scu-PA and uses of the tcu PA of this invention.

EXAMPLE 1

Preparation of thrombin cleaved scu-PA—Method 1

In a specific embodiment of this invention, scu-PA (prourokinase) is obtained from human kidney cells (Kohno, T., Hopper, P., Lillquist, J. S., Suddith, R. L., Greenlee, R., and Moir, D. T. 1984. Biotechnology, 2, 628–634). The 156-phenylalanine 157 peptide bond of the scu-PA is cleaved by thrombin in the following manner. The reaction mixture (18 ml) contains 50 mM Tris-HCl (pH 7.4), 0.15M sodium chloride, 100 units thrombin (from human plasma, T-6759, Sigma Chemical Co., St. Louis, Mo.) per mg of scu-PA, and 3 to 6 mg of scu-PA. The mixture is incubated for one hour at 37 degrees C. Cleavage of scu-PA by thrombin is stopped by the addition of an excess of hirudin (110 units per mg of scu-PA), obtained from Sigma Chemical Co. (H-4256), and chilling on ice. To confirm that cleavage by thrombin is complete, the reaction mixture is analyzed by SDS polyacrylamide gel electrophoresis (Laemmli, U. K. 1970. Nature 227, 680) followed by silver staining (Heukeshoven, J., and Dernick, R. 1985. Electrophoresis 6, 103–112).

EXAMPLE 2

Preparation of thrombin cleaved scu PA—Method 2

Thrombin sepharose is prepared in the following manner. 0.6 grams of cyanogen bromide activated sepharose (Pharmacia) is swelled in 50 ml of 1 mM HCl for 15 minutes and then washed with 100 ml of 1 mM HCl. Two vials of thrombin (1110 units/vial, 3313 units/mg, Sigma #T-6759) are each rehydrated with 1.0 ml of distilled water. The contents of the rehydrated vials are combined and added to 2 ml of coupling buffer (0.1M sodium bicarbonate, 0.5M NaCl, pH 8.3). The swelled resin is washed with 10 ml of coupling buffer and transferred to the thrombin solution. The thrombin/resin mixture is incubated on a rocking platform at room temperature for 2 hours. At the end of the incubation, resin is separated from the solution by filtration then transferred to a solution of 0.2M glycine pH 8.0. The mixture is mixed gently at 4 degrees C. for 16 hours. The resin is washed extensively with coupling buffer, resuspended in 4 ml of coupling buffer, and then stored at 4 degrees C.

The amount of active thrombin coupled to the resin is quantitated using the chromogenic substrate S-2238 (peptide paranitroanilide, Kabi Vitrum, Stockholm, Sweden). Aliquots (5 or 10 ul) are incubated in 50 mM Tris-HCl (pH 8.3), 38 mM NaCl, and 1 mM S-2238 in a volume of 1 ml for 10 minutes at 37 degrees C. 0.1 ml of 50% acetic acid is then added to stop the reaction and the absorbance at 405 nm determined. A standard curve, constructed by plotting the concentration of a thrombin standard versus the absorbance at 405 nm obtained, is used to calculate the amount of thrombin present in the samples of resin. The resin contains 140 units of thrombin per ml.

The arg 156-phe157 peptide bond of scu-PA obtained from human kidney cells (as in example 1 above) is cleaved by thrombin in the following manner. Reaction mixtures contain 50 mM Tris-HCl (pH 7.4), 0.15M sodium chloride, thrombin sepharose (prepared as described above) and scu PA (1 mg). The mixtures are incubated for one-two hours at 37 degrees C. Cleavage of scu-PA by thrombin is stopped by removing the thrombin sepharose from the reaction mixture. This is accomplished by centrufugation of the reaction mixture at 2000×g for 15 minutes. The supernatant containing the thrombin cleaved scu-PA is aspirated and stored at 4 degrees C. The resin pellet is saved for future use.

To confirm that cleavage by thrombin has gone to completion the reaction mixture is analyzed by two methods. (1) an aliquot is reduced with dithiothreitol and analyzed by SDS polyacrylamide gel electrophoresis (Laemmli, U. K., *Nature* 227, 680, 1970) and silver staining (Heukeshoven, J. and Dernick, R., *Electrophoresis* 6, 103-112, 1985). This demonstrates that scu-PA is converted completely to a two chain molecule by thrombin. (2) The amidolytic activity of the thrombin treated scu-PA is quantitated in a 1 ml reaction containing 0.1 ml of thrombin treated scu-PA, 0.1 ml of 3 mM S-2444 (pyro GLU-GLY-ARG-para-nitroanilide; Kabi Vitrum, Stockholm, Sweden), 0.8 ml of 50 mM Tris-HCl (pH 8.8), and 38 mM NaCl and 0.1% polyethylene glycol. The reaction mixtures are incubated at 37 degrees C. for 5 minutes, then stopped by the addition of 0.1 ml of 50% acetic acid, and the absorbance at 405 nm determined. Amidolytic acitivity of the sample is calculated based on the standard curve generated using urinary urokinase as a standard. The amidolytic activity of the thrombin-cleaved scu-PA is less than 1000 IU/mg (protein concentration determined using the method of Lowry).

EXAMPLE 3

Plasminogen Activation in vitro Catalyzed by Thrombin-generated tcu-PA

The activation of the N-terminal glu form of plasminogen by thrombin-generated tcu-PA is measured essentially according to the kinetic assay for measuring plasminogen activation by scu-PA, described by Collen, et al. (Collen, et al., *J. Biol Chem.* 261, 1253-1258, 1986). Reaction mixtures containing 50 mM Tris-HCl (pH 7.4), 38 mM NaCl, 0.01% Tween 80, 1.1 mM S-2251 (H-D-VAL-LEU-LYS-para-nitroanilide; Kabi Vitrum, Sweden), 5 nM thrombin-cleaved scu-PA, and glu-plasminogen (2-75 uM) are incubated at 37 degrees C. in a thermostat controlled recording spectrophotometer. Absorbance at 405 nm is monitored at 30 second intervals and plotted as a function of time. The slope of this absorbance curve (i.e., the rate of change of color generation in the reaction) at various times is plotted versus time. The slope of this curve corresponds to the amount of plasmin generated from glu-plasminogen. Levels of plasmin generated in the reaction mixture are quantitated by comparing these slopes to the slopes generated with known quantitites of a plasmin standard. Initial rates of plasmin generation were used to calculate the kinetic constants Km and k2 using the Eisenthal, Cornish-Bowden method (Biochem J. 139, 715-720, 1974). Using this method Km=10 uM and k2=0.006 per sec. Thus, thrombin generated tcu-PA is an effective activator of glu-plasminogen in vitro.

EXAMPLE 4

Fibrinolysis in vivo Initiated by Thrombin-generated tcu-PA

The rabbit jugular vein thrombolysis model system (Collen, D., Stassen, J. M., and Verstraete, M. 1983. *J. Clin. Invest.* 71, 368-376) is used to determine the thrombolytic activity of scu-PA cleaved by thrombin. Blood clots made with $^{125}$I-labelled fibrinogen (Amersham) are introduced into the external jugular vein of New Zealand white rabbits. Scu-PA which was cleaved with thrombin is infused into the rabbits over a period of four hours through the marginal ear vein. Thirty minutes after the end of the infusion, the clots are surgically removed from the animals and the radioactivity remaining in the clot is counted in a gamma counter. Lysis values are calculated and expressed as percent of the clot lysed.

Blood samples (0.2 ml) are removed from each animal immediately before the start of the infusion and at the end of the infusion by using a catheter placed in the femoral artery. The samples are added to 0.2 ml of 0.1M trisodium citrate, and plasma is prepared by centrifugation at 2000×g for 15 minutes to remove the blood cells. The plasma samples may be stored frozen at −70 degrees C. for up to 6 months before analysis. The fibrinogen content of each sample is determined by the method of Vermylen, et al. (1963, *Clin. Chim. Acta* 8: 418-424) and the alpha-2-antiplasmin content is measured according to the method of Edy et al. (1976, *Throm. Res.* 8: 513-515).

A typical dose response derived from testing three dosages of thrombin-cleaved scu-PA (0.5 mg/kg, 1.0 mg/kg, and 2.0 mg/kg) is shown in Table 1. Lysis values ranged from 9±2.6% for the 0.5 mg/kg dose to 25±3.0% for the 2.0 mg/kg dose. Fibrinogen and alpha-2-antiplasmin levels present in the rabbits at the end of the infusion of thrombin-cleaved scu-PA are also shown in Table 1. Fibrinogen and alpha-2-antiplasmin levels did not decrease significantly, indicating that the clot lysis mediated by thrombin-generated tcu PA is fibrin-specific. For comparison, three dosages of scu-PA and four dosages of plasmin-cleaved scu-PA were also tested, and the data are included in Table 1. Clearly, judging from the sparing of fibrinogen and alpha-2-antiplasmin, thrombin-cleaved scu-PA is on par with or superior to scu-PA in its fibrin specificity of clot lysis. Both molecules exhibit much more fibrin specificity than plasmin-cleaved scu-PA. These data are shown graphically in FIG. 2.

TABLE 1. Clot lysis and residual fibrinogen and alpha-2-antiplasmin levels in rabbits treated with scu PA, thrombin-cleaved scu PA and plasmin-cleaved scu PA.

Figure 2:
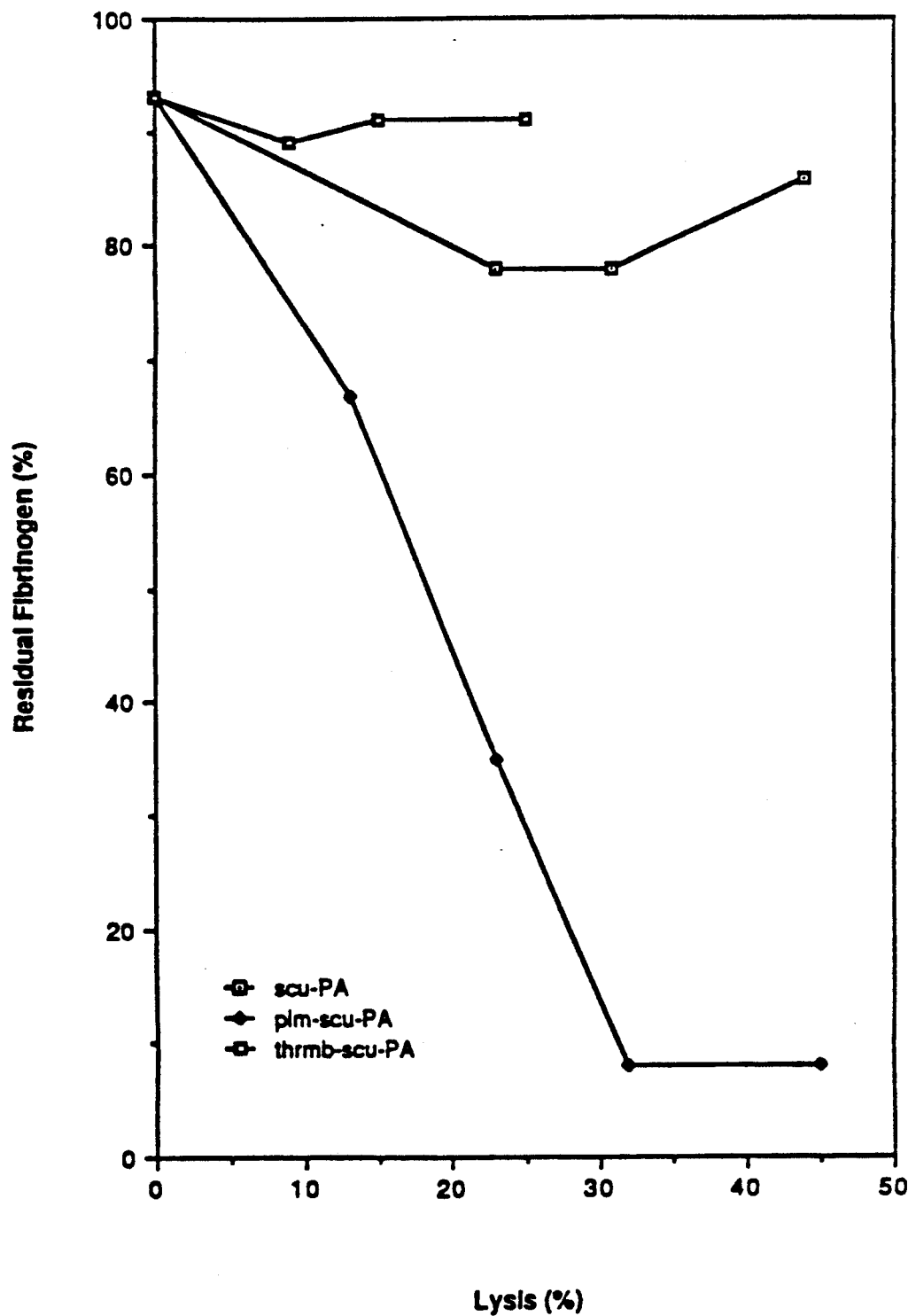

FIG. 2 shows the effect of in vivo thrombolysis induced by thrombin cleaved scu-PA at arginine 156, scu-PA, and plasmin cleaved scu-PA at residue 158, on plasma fibrinogen levels. Thrombin-cleaved scu-PA and plasmin-cleaved scu-PA were tested for the ability to mediate lysis of $^{125}$I-labeled fibrin clots in vivo using the rabbit jugular vein thrombolysis model system (Collen, D. et al. J. Clin. Invest. 71: 368–376, 1983). Doses ranging from 0.5 to 3.0 mg/kg were administered to the rabbits over a period of four hours. The extent of clot lysis (expressed as %) was determined after an additional 30 minutes. Plasma samples taken from the rabbits at the beginning and at the end of the infusion were assayed for clottable fibrinogen (Vermylen, C. et al. Clin Chem Acta 8: 418–424, 1963). Fibrin levels at the end of the infusion expressed as percentage of that present at the beginning of the infusion, are plotted as a function of clot lysis. This is a graphical representation of the clot lysis and residual fibrinogen data shown in Table 1, and each point is an average from the number of rabbits shown in Table 1. Abbreviations are as follows: thrmb-scu-PA is thrombin-cleaved scu-PA, and plm scu-PA is plasmin cleaved scu-PA.

While a fibrin specific two-chained urinary plasminogen activator derived by forming cleavage at the 156–157 amino acid has been described, other fibrin specific urinary two-chain plasminogen activators are also useful. For example, fibrin specific two-chain plasminogen activators in which the amino acid residues as shown in FIG. 1 can be deleted at one or more of positions 1 to 147 can be used to dissolve clots in vivo in accordance with this invention. Thus, amino acid residue 1–146 or any part of them can be deleted.

The plasminogen activator of this invention can have an amino terminal residue of a new chain which begins at any of the amino acid residues 149–157 instead of at residue 156 in the chain shown in FIG. 1. The scu-PA plasminogen activator can be cleaved at amino acids 149–157 directly by suitable enzymes or, alternately any of these amino acids can be replaced with others and then the chain can be cleaved at the replacement site. Recombinant DNA procedures can be used to replace amino acids to enable DNA of cleavage at sites 149–157. In the preferred embodiment two-chain plasminogen activator is provided in which proteolysis is accomplished at the arginine 156-phenylalanine 157 peptide bond of scu-PA by means of human thrombin. However, other enzymes with similar substrates specificities can be used to carry out cleavage in place of thrombin. Proteolytic cleavage of single chain urinary plasminogen activator derived by recombinant methods or from prourokinase from mammalian or other cells such as kidney cells, can be useful in this invention. In all cases, the fibrin specific two-chain plasminogen activator is used at a dosage level sufficient to dissolve clots in the body without causing unwanted changes to the body.

TABLE 1

Clot lysis and residual fibrinogen and alpha-2-antiplasmin levels in rabbits treated with scu-PA, thrombin-cleaved scu-PA or plasmin-cleaved scu-PA

| Dose (mg/kg) | Lysis (%) | Fibrinogen (% of Initial) | Antiplasmin (% of Initial) |
|---|---|---|---|
| 0 | 7.8 +/− 1.3 (6) | 92 +/− 7.2 (3) | 96 +/− 3.0 (3) |
| *thrombin-cleaved scu-PA:* | | | |
| 0.5 | 9.0 +/− 2.6 (3) | 89 +/− 5.1 (3) | 95 +/− 6.1 (3) |
| 1.0 | 15.0 +/− 2.9 (5) | 91 +/− 8.1 (3) | 94 +/− 7.6 (3) |
| 2.0 | 25.0 +/− 3.0 (4) | 91 +/− 15 (3) | 92 +/− 9.1 (3) |
| *plasmin-cleaved scu-PA* | | | |
| 0.5 | 13.0 +/− 1.4 (4) | 67 (1) | 51 (1) |
| 1.0 | 23.0 +/− 0.9 (3) | 35 +/− 12 (3) | 31 +/− 11 (3) |
| 2.0 | 32.0 +/− 0.9 (3) | 7.6 +/− 2.1 (3) | 14 +/− 2.3 (3) |
| 3.0 | 45.0 +/− 2.0 (3) | 7.7 (1) | 11 (1) |
| *scu-PA* | | | |
| 0.5 | 23.0 +/− 1.2 (3) | 78 +/− 4.5 (3) | 93 +/− 2.5 (3) |
| 1.0 | 31.0 +/− 0.7 (3) | 78 +/− 1.0 (3) | 76 +/− 2.0 (3) |
| 2.0 | 44.0 +/− 2.1 (3) | 86 (1) | 92 (1) |

Fibrinogen and alpha-2-antiplasmin levels are expressed as a percentage of the levels present at the start of the infusion. The number of rabbits analyzed is given in parentheses following the value obtained. These data are shown graphically in FIG. 2.

We claim:

1. A composition comprising a therapeutically effective concentration of a fibrin specific two-chain urokinase type plasminogen activator, said activator being derived by proteolysis at the arginine 156-phenylalanine 157 peptide bond of scu-PA, in admixture with a pharmacologically acceptable excipient.

2. The composition in accordance with claim 1 wherein said proteolysis is carried out by cleavage with thrombin.

3. A composition in accordance with claim 1 wherein said concentration is from about 0.1 mg/ml to about 10 mg/ml.

4. A method of treatment of thrombosis in a mammalian host which comprises administering to said host an appropriate amount of the composition of claim 1.

5. A method in accordance with the method of claim 4 wherein said treatment is carried out by intravenous injection.

6. A method in accordance with the method of claim 10 wherein said dosage level is from about 1.0 to about 4.0 mg per kilogram of body weight administered for a period of up to six hours.

7. A method of treatment of thrombosis in a mammalian host which comprises administering to said host an effective amount of a fibrin-specific two-chain urokinase type plasminogen activator, said activator being derived by proteolysis at the arginine 156–phenylalanine 157 peptide bond of scu-PA.

* * * * *